(12) United States Patent
Kramer et al.

(10) Patent No.: US 9,974,520 B2
(45) Date of Patent: May 22, 2018

(54) URINE SAMPLE COLLECTION APPARATUS

(71) Applicants: Heidi Kramer, Monroe, NY (US);
Herman Wagschal, Monroe, NY (US);
Joseph Wagschal, Monroe, NY (US)

(72) Inventors: Heidi Kramer, Monroe, NY (US);
Herman Wagschal, Monroe, NY (US);
Joseph Wagschal, Monroe, NY (US)

(73) Assignee: WK HOLDINGS, INC., Monroe, NY (US)

( * ) Notice: Subject to any disclaimer, the term of this patent is extended or adjusted under 35 U.S.C. 154(b) by 17 days.

(21) Appl. No.: 14/704,034

(22) Filed: May 5, 2015

(65) Prior Publication Data

US 2015/0320404 A1    Nov. 12, 2015

Related U.S. Application Data

(60) Provisional application No. 61/989,210, filed on May 6, 2014.

(51) Int. Cl.
*A61B 10/00* (2006.01)
*A61B 90/90* (2016.01)

(52) U.S. Cl.
CPC ............ *A61B 10/007* (2013.01); *A61B 90/90* (2016.02)

(58) Field of Classification Search
None
See application file for complete search history.

(56) References Cited

U.S. PATENT DOCUMENTS

| | | | |
|---|---|---|---|
| 3,571,817 A * | 3/1971 | Gosnell | A61B 10/007 4/144.1 |
| 5,105,824 A | 4/1992 | Rasch | |
| 5,410,471 A * | 4/1995 | Alyfuku | A61B 5/117 4/314 |
| 5,652,911 A | 6/1997 | Van Venrooy et al. | |

(Continued)

FOREIGN PATENT DOCUMENTS

| | | |
|---|---|---|
| WO | 199618373 A1 | 7/1995 |
| WO | 199523337 A1 | 8/1995 |

(Continued)

OTHER PUBLICATIONS

International Search Report for International Application No. PCT/US2015/060181 (dated Feb. 3, 2016).

*Primary Examiner* — Matthew Kremer
(74) *Attorney, Agent, or Firm* — Merchant & Gould P.C.

(57) ABSTRACT

An apparatus and method for automatically collecting urine samples from a patient are described. The apparatus includes a toilet bowel with a reservoir and a urine collection receptacle that is a flexible heat sealable plastic bag in an enclosure mounted exterior to the reservoir. The receptacle can be rotated into the toilet reservoir to collect urine and removed therefrom by rotating it back into the enclosure. The opening to the bag is then heat sealed to produce a urine sample packet. The receptacle may be automatically divided into a plurality of urine sample packets by heat sealing the bag at several locations along its length and then cutting the bag at the appropriate heat sealed locations. Each packet is then printed with patient indicia. The sample packets then pass through an opening in the enclosure for removal and subsequent analysis. An electrical activation interface is provided to control the process.

10 Claims, 8 Drawing Sheets

(56) References Cited

U.S. PATENT DOCUMENTS

| | | |
|---|---|---|
| 5,714,033 A | 2/1998 | Hayashi et al. |
| 5,720,054 A | 2/1998 | Nakayama et al. |
| 5,730,149 A * | 3/1998 | Nakayama ............ A61B 10/007 |
| | | 600/573 |
| 5,920,916 A | 7/1999 | Norton |
| 6,052,842 A | 4/2000 | He |
| 6,294,046 B1 | 9/2001 | Kume et al. |
| 6,358,477 B1 | 3/2002 | Webb et al. |
| 6,402,702 B1 * | 6/2002 | Gilcher ............ A61B 10/0291 |
| | | 600/562 |
| 6,493,884 B1 | 12/2002 | Muller et al. |
| 6,572,564 B2 | 6/2003 | Ito et al. |
| 6,684,414 B1 | 2/2004 | Rehrig |
| 6,775,852 B1 | 8/2004 | Alvarez et al. |
| 6,852,288 B2 | 2/2005 | Newberg |
| 7,195,602 B2 | 3/2007 | Yong et al. |
| 7,229,409 B2 | 6/2007 | Ito et al. |
| 7,291,309 B2 | 11/2007 | Watson et al. |
| 7,454,881 B2 | 11/2008 | Hanatani et al. |
| 7,785,304 B2 | 8/2010 | Kashmiran et al. |
| 7,819,821 B2 | 10/2010 | Forte |
| 7,846,384 B2 | 12/2010 | Watson et al. |
| 8,328,733 B2 | 12/2012 | Forte et al. |
| 8,690,794 B1 | 4/2014 | Gallardo |
| 9,149,163 B2 | 10/2015 | Matt et al. |
| 9,155,525 B2 | 10/2015 | Lipinsky et al. |
| 2002/0193762 A1 | 12/2002 | Suydam |
| 2005/0004538 A1 | 1/2005 | Forte |
| 2005/0142041 A1 | 6/2005 | Newberg |
| 2005/0261605 A1 | 11/2005 | Shemer et al. |
| 2007/0006368 A1 | 1/2007 | Key |
| 2007/0044213 A1 | 3/2007 | Hall |
| 2007/0270716 A1 | 11/2007 | Wu et al. |
| 2009/0089919 A1 | 4/2009 | Rudolph |
| 2009/0216099 A1 | 8/2009 | Kim |
| 2009/0255045 A1 * | 10/2009 | Sakurai ............ A47K 11/026 |
| | | 4/484 |
| 2010/0269250 A1 | 10/2010 | Wilson et al. |
| 2010/0288059 A1 | 11/2010 | Viljoen et al. |
| 2011/0051125 A1 | 3/2011 | Kim |
| 2011/0139276 A1 | 6/2011 | Kashmiran et al. |
| 2012/0046574 A1 | 2/2012 | Skakoon |
| 2013/0139474 A1 | 6/2013 | Coleman |
| 2014/0216598 A1 | 8/2014 | Kashmirian et al. |
| 2014/0276214 A1 | 9/2014 | Lipinsky et al. |
| 2015/0223783 A1 | 8/2015 | Eschete et al. |
| 2015/0320404 A1 | 11/2015 | Kramer |

FOREIGN PATENT DOCUMENTS

| | | | |
|---|---|---|---|
| WO | 199609794 A1 | 4/1996 | |
| WO | 199708993 A2 | 3/1997 | |
| WO | 199727795 A1 | 8/1997 | |
| WO | 199928724 A1 | 6/1999 | |
| WO | 199959874 A1 | 11/1999 | |
| WO | 200209493 A1 | 2/2002 | |
| WO | 2002026096 A1 | 4/2002 | |
| WO | 2002094104 A1 | 11/2002 | |
| WO | 2003007771 A1 | 1/2003 | |
| WO | 2004036343 A2 | 4/2004 | |
| WO | 2005048842 A1 | 6/2005 | |
| WO | 2007009170 A1 | 1/2007 | |
| WO | 2008065325 A1 | 6/2008 | |
| WO | 2009107988 A2 | 9/2009 | |
| WO | WO 2009129638 A2 * | 10/2009 | ........... A47K 11/026 |
| WO | 2010132800 A1 | 11/2010 | |
| WO | 2011113164 A2 | 9/2011 | |
| WO | 2011144950 A1 | 11/2011 | |
| WO | 2012011127 A1 | 1/2012 | |
| WO | 2014152626 A2 | 9/2014 | |
| WO | 2016178711 A1 | 11/2016 | |

* cited by examiner

Overview 2

Position 1

Position 2

Collecting the urine.

Preparing the urine sample packets.

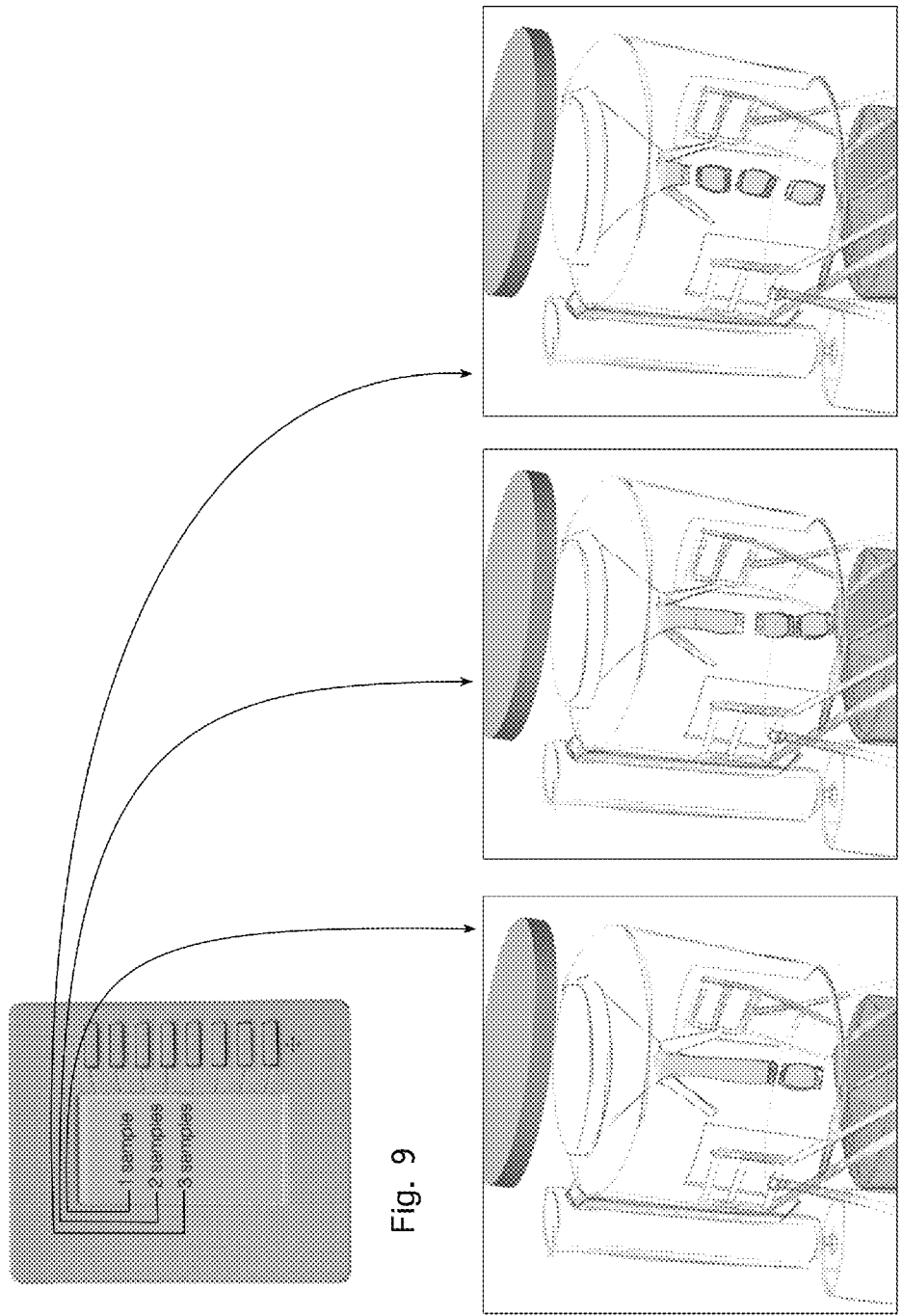

Labeling and dispensing the urine sample packets.

Resetting of the hi-tech urine sample collector toilet.

URINE SAMPLE COLLECTION APPARATUS

RELATED APPLICATIONS

This application is a Non-Provisional Patent Application claiming priority of Provisional Patent Application 61/989,210 filed on May 6, 2014, the entire disclosure of this application is incorporated herein by reference.

BACKGROUND OF THE INVENTION

Field of the Invention

This invention relates to an apparatus and method for automatically collecting a urine sample from a patient, dividing the sample into a plurality of urine sample packets and transporting them to a clinical laboratory for analysis.

Description of the Related Art

Applicant is aware of the following relevant US Patent references:

U.S. Pat. No. 5,184,359 A to Tsukamura discloses a toilet urine analysis system consisting of a toilet bowl and analysis machine with pushbuttons and display adjacent to the toilet bowl and a sample taking apparatus that uses disposable collection units that are automatically disposed of after each use by mechanical arm.

U.S. Pat. No. 5,062,304 A to Van Buskirk discloses a disposable urine collection unit that fits inside a toilet bowl and that is connected to a chemical analysis machine. The sample may be removed and sent to a laboratory.

U.S. Pat. No. 4,554,687 A to Carter discloses a urine analysis system for a toilet bowl that consists of a disposable urine collection unit that fits inside the toilet bowl and that is connected by a line to an analysis computer.

U.S. Pat. No. 8,147,406 B2 to Kawamura discloses a system of urine analysis that consists of a toilet bowl having a urine collection component that is connected to a urine analysis machine.

U.S. Pat. No. 7,229,409 B2 to Ito discloses a urine analysis system connected to a toilet.

U.S. Pat. No. 5,720,054 A to Nakayama discloses a urine sample kit that is integral to a toilet.

U.S. Pat. No. 5,111,539 A to Hiruta discloses a toilet device with system for inspecting health conditions.

US 2007/0006368 A1 to Key discloses a disposable funnel shaped urine collection device.

US 2005/0261605 A1 to Shemer discloses a system for monitoring the health of an individual that includes a collection device that fits inside a toilet bowl and that is connected to an analysis device.

SUMMARY OF THE INVENTION

This invention is directed to a urine sample collection system that is integral with a toilet system. The system is fully automated to produce one or plurality, e.g., from 1-3, of sealed urine sample packets for further processing and analysis in the laboratory.

The apparatus includes a toilet bowel with a reservoir and a urine collection receptacle that is a flexible heat sealable plastic bag. The bag is in an enclosure mounted exterior to the reservoir. The receptacle can be activated to automatically rotate into the toilet reservoir to collect urine and then removed therefrom by rotating it back into the enclosure. The opening to the bag is then heat sealed to produce a urine sample packet. The receptacle may be automatically divided into a plurality of urine sample packets by heat sealing the bag at several locations along its length and then cutting the bag at the appropriate heat sealed locations. Each packet is then printed with patient indicia. The sample packets then pass through an opening in the enclosure for removal and subsequent analysis. An electrical activation interface is provided to control the process.

DESCRIPTION OF THE INVENTION

FIG. 1 and FIG. 2

Referring to FIGS. 1 and 2, the collection system may be used as the regular, well known toilet system, e.g., toilet bowl. When used in this manner, no urine samples are collected.

As shown in FIGS. 2-14, the collection system is structured and functions to collect one or a plurality of urine sample packets. The collection system goes through several steps to collect from a patient sitting on the bowl at least one, and preferably a plurality of sealed urine sample packets that are labeled with patient information.

FIG. 3 is perspective of the urine collection system of this invention referencing the parts of the invention, the parts being color coded in the Figures:

Toilet seat: This is the seat the patient sits on for conventional use of the urine collection system as a toilet and for the collection of urine.

Regular toilet reservoir: This is a bowel for collecting waste materials when used in the conventional manner. Although not shown, this may be hooked up to the toilet system in the room in which the collection system is situated.

Dispenser for urine collection: This is initially positioned in front of the toilet seat as depicted in FIGS. 3 and 4.

Urine collection receptacle: This is a receptacle for receiving the Disposable urine collector and any overflow of urine.

Disposable urine collector: This is a disposable container, preferable a flexible heat sealable, plastic bag that directly receives the urine.

Door for dispensed urine collector: This is a door in the side of the collector system that permits selective access to the interior and removal of the specimen urine sample packets from the collector system.

Ramp for dispensing the urine collector: After the disposable urine collector is sealed into urine sample packets and a printed label adhered thereto, it exits through this ramp to the door.

Trash for discarded disposable urine collection: A receptacle for the disposable packaging material from the disposable urine collector.

Labeling printer: positioned and integrated into the collection system to print critical patient data on the specimen urine packets.

Seal & Cut arms: These are the means for cutting and sealing the disposable urine collector packaging into sample sized sealed specimen urine sample packets for shipment to the laboratory.

FIG. 4 depicts the interior structure of the urine collection system. In this position, the urine collection receptacle (A) is outside the toilet reservoir (B). The edge of the urine collection receptacle (C) creates a water tight seal with the toilet reservoir so that the toilet can be flushed without water leaking out.

FIG. 5 depicts an electronic interface that is integrated into the collection system. The electronic interface activates the collection system and the steps that are part of the process for collecting and "packaging" the urine sample. The electronic interface may be wall mounted near the collection system or on a wall outside the area, e.g., hard wired, where the collection system is located. The collection system may also be activated through an internet and/or Wi-Fi interface, e.g., an "App" for an I-phone or I-Pad or through a desk top computer program.

As shown in FIGS. 4 and 6, the system has a first area 50, a second area 52, and a rotating shaft 60 adapted to move the urine collection receptacle (A) between the first area 50 and the second area 52.

FIG. 6 depicts the urine collection system just prior to collecting urine. The urine collector receptacle is rotated into the toilet's reservoir (D). The disposable urine collector is positioned directly under the toilet seat (E) to collect the patient's urine.

Referring to FIGS. 7 and FIGS. 7a-7c:

Figure 2:
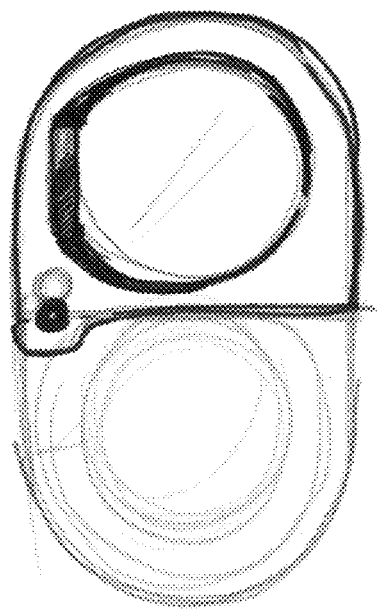
Figure 1:
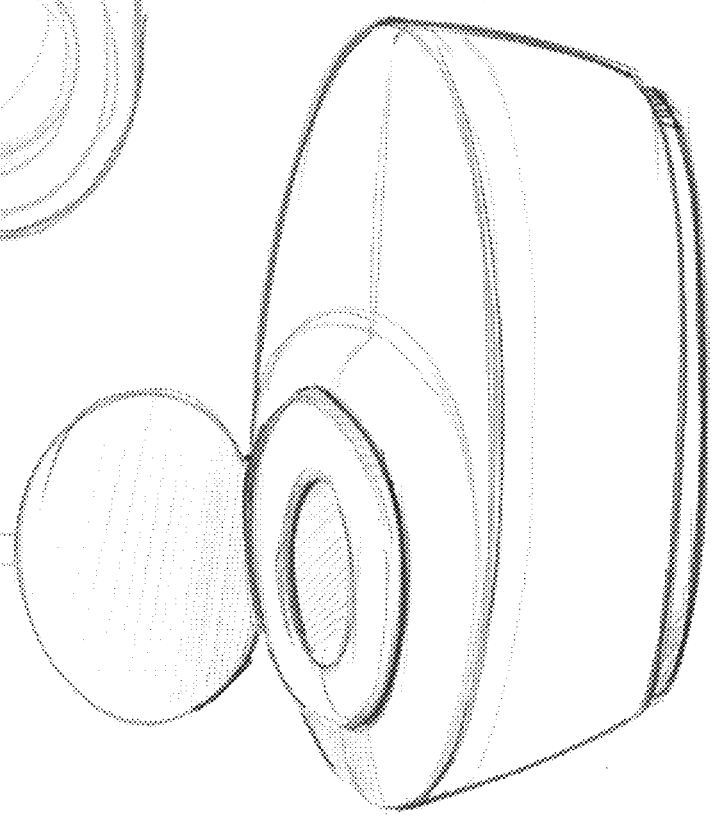
Figure 3:
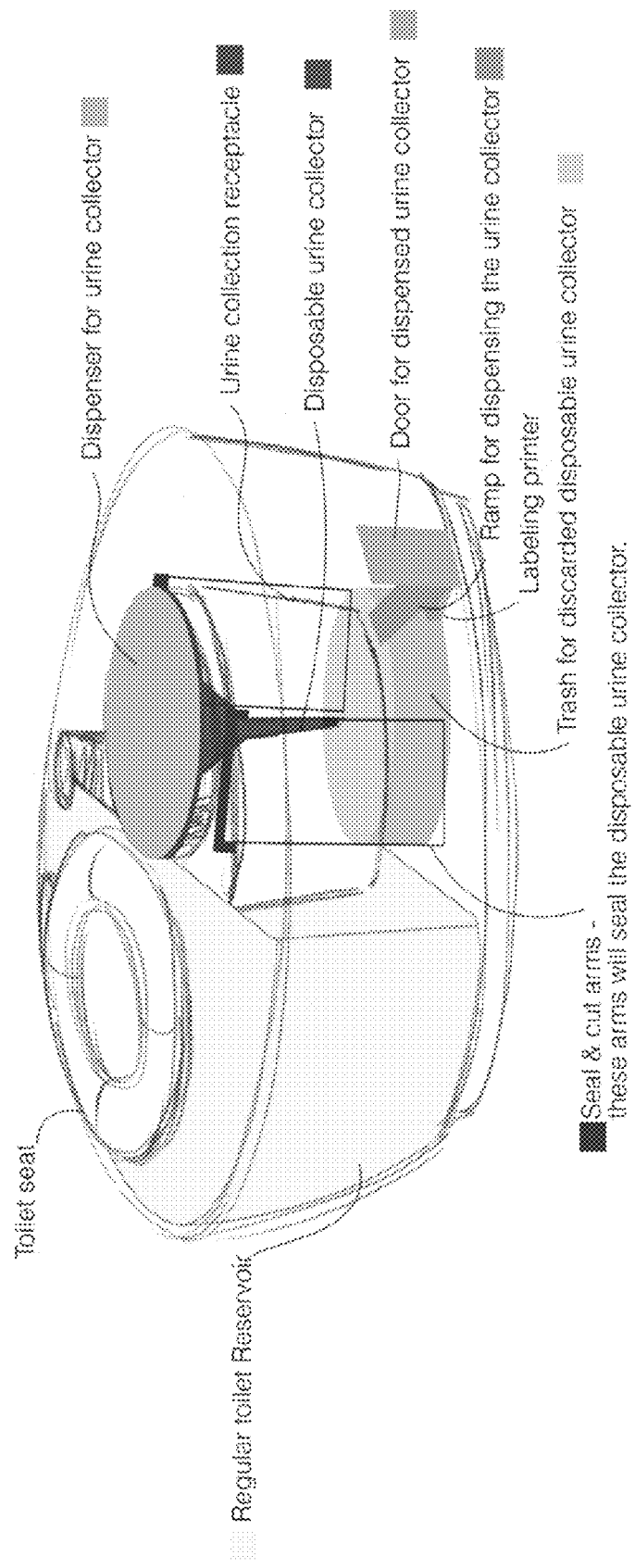
Figure 4:
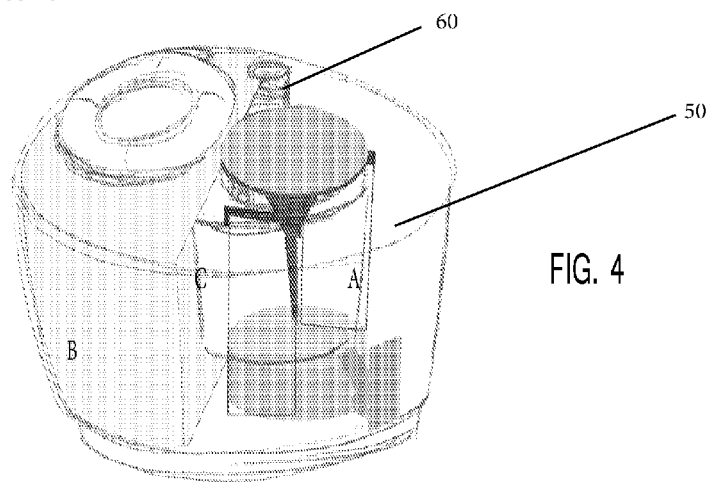
Figure 5:
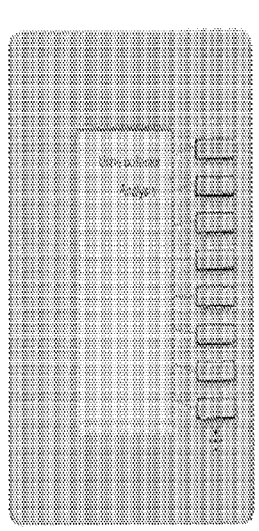
Figure 6:
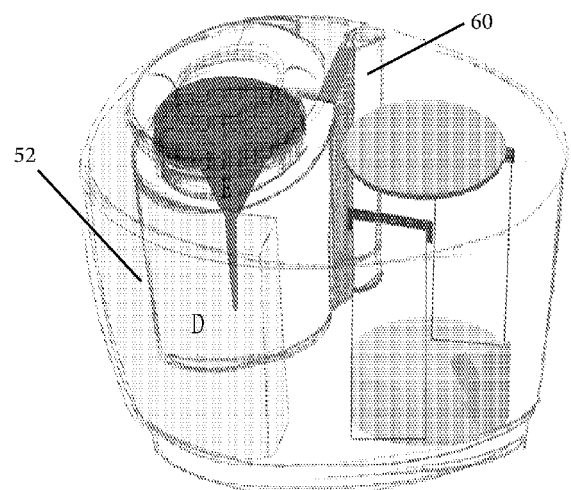
Figure 7:
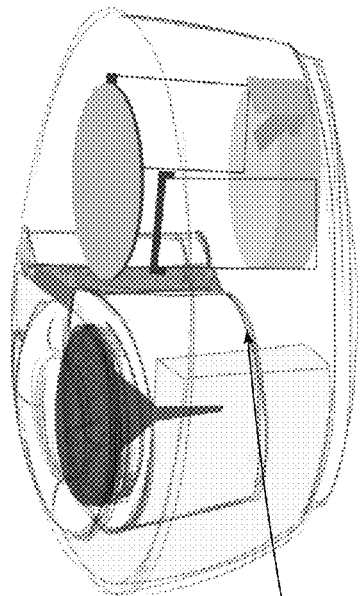
FIG. 7a depicts the urine collector receptacle moved into position in the toilet reservoir and the disposable urine collector positioned directly under the toilet seat. The urine falls into the disposable urine collector.
FIG. 7b depicts the disposable urine collector having built in drain spouts (F) to drain any excess urine into the water in the toilet reservoir.
FIG. 7c depicts the disposable urine collector after the excess urine flows out and there remains a predetermined amount of urine therein.
Figure 7C:
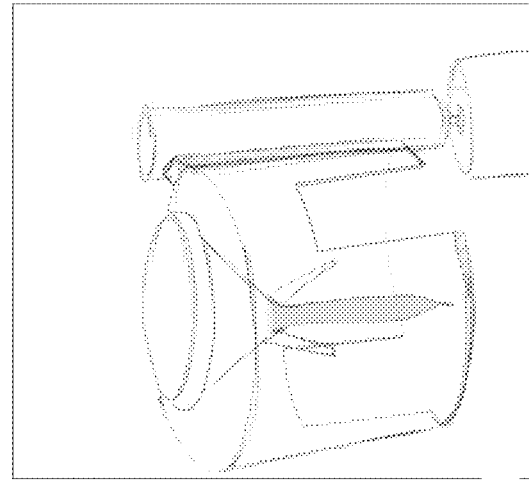
Figure 7B:
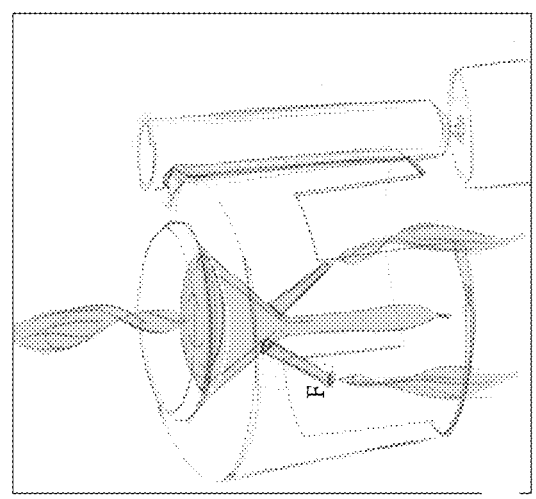
Figure 7A:
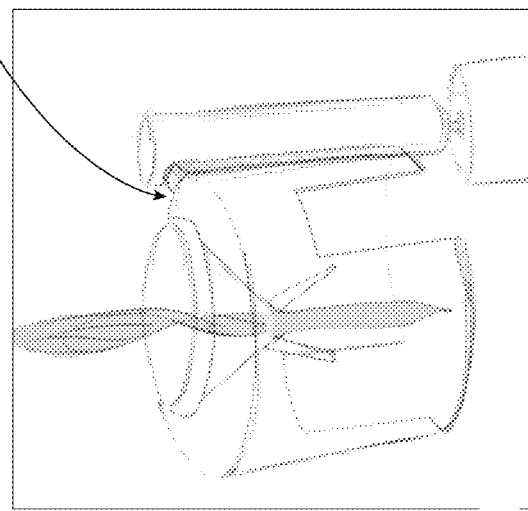
Figure 8:
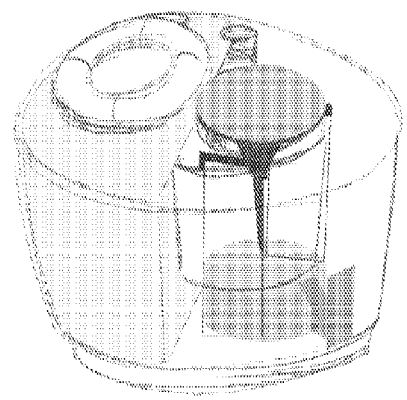
Figure 8A:
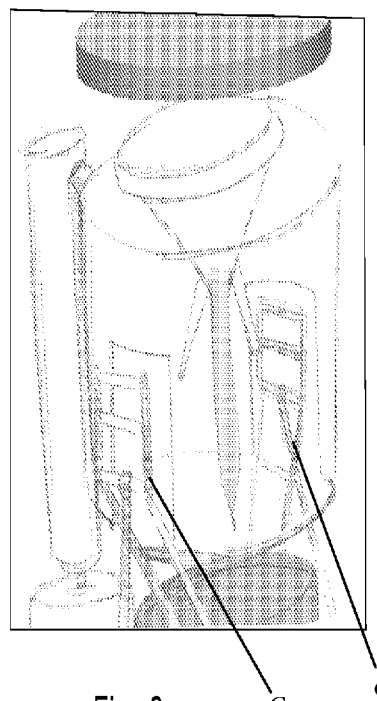
Figure 8B:
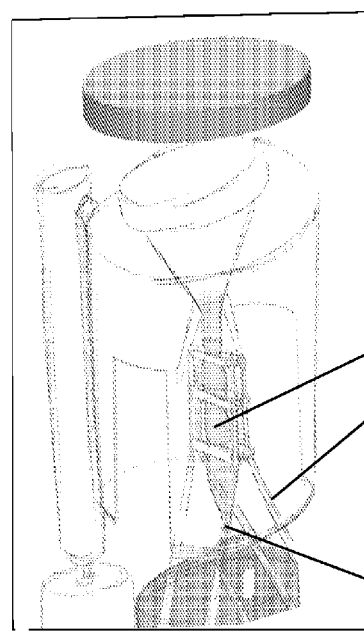

Referring to FIGS. 8 and FIGS. 8a and 8b:

FIG. 8a depicts the urine collector receptacle rotated back to its initial position (as in FIG. 8) with the predetermined amount of urine in the disposable urine collector.

FIG. 8b depicts a means for sealing and cutting the disposable urine collector into one or more urine sample packets. As depicted, sealing & cutting arms (G) close onto the disposable urine collector. The dispenser ramp moves under the disposable urine collector (H)

Figure 10:
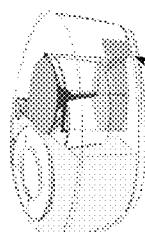

FIGS. 9 and 9a, 9b and 9c through the electronic interface, as depicted in this example, the technician has the option of choosing through the interface, one, two or three urine sample packets to be sealed and cut from the disposable urine collector. The urine sample packets are then dropped onto the dispenser ramp and subsequently passed through the door, see FIG. 10. This invention envisions that any number of urine sample packets can be made, although a maximum of three are depicted in this embodiment.

Figure 10B:
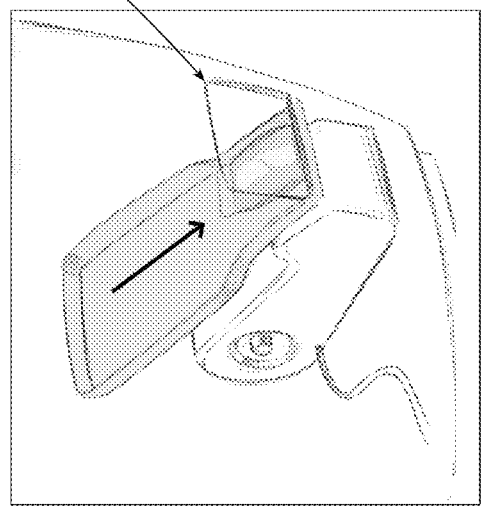
Figure 10C:
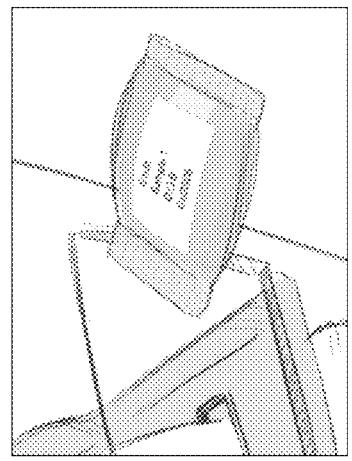
Figure 10A:
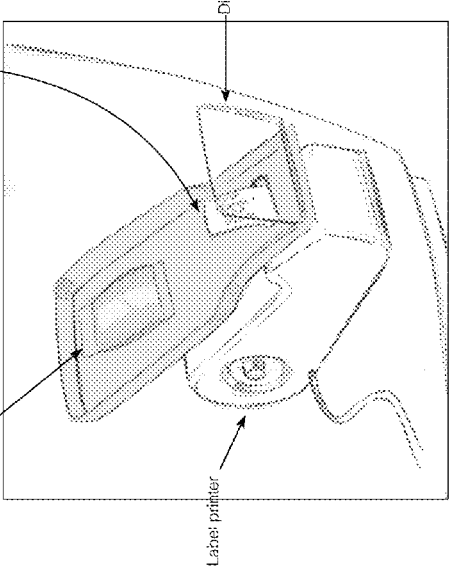

FIGS. 10 and FIGS. 10a-c depict the labeling and dispensing of the urine sample packets:

FIG. 10a depicts the urine sample packet falling onto the dispenser ramp juxtaposed over the label printer.

FIG. 10b depicts the urine sample packet sliding down the ramp and over a printed label having an adhesive backing that adheres to the packet.

FIG. 10c depicts the final (hermetically) sealed urine sample packet having the printed label on the packet with the relevant patient information ready to be sent to the laboratory for testing.

FIG. 11-14 depicts resetting the urine collection system to enable another test process to take place.

Figure 11:
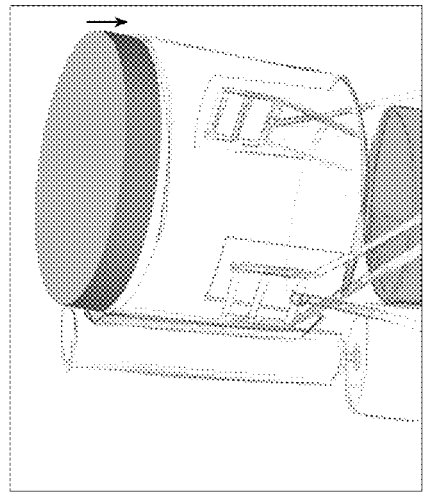

FIG. 11 depicts the dispenser ramp moved out of position. The holding mechanisms of the disposable urine collector (I) releases and drops the remainder of the disposable urine collector into the trash receptacle (J).

Figure 12:
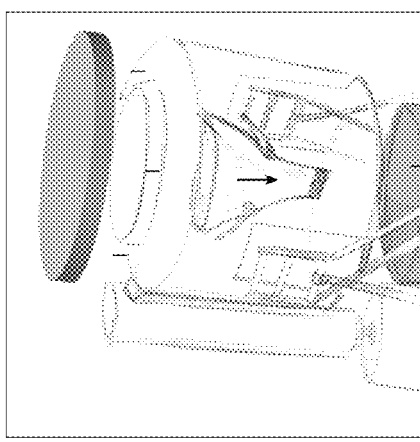

FIG. 12 depicts the disposable urine collector loader moves down and installs the next sterile disposable urine collector.

Figure 13:
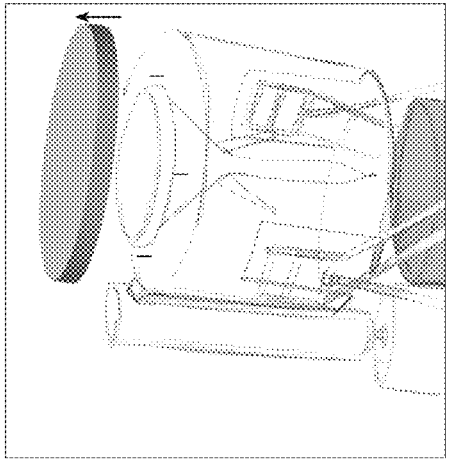

FIG. 13 depicts the holding mechanisms (I) of the disposable urine collector engaged to hold it in place. The loader moves back up.

Figure 14:
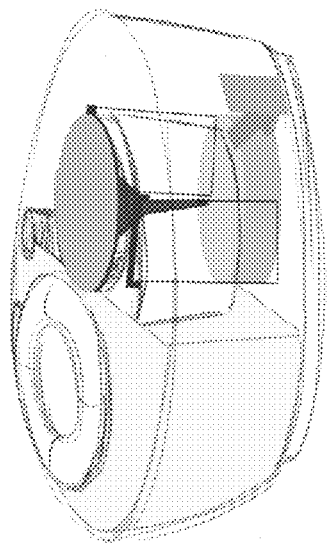

FIG. 14 depicts the urine collection system repositioned for the next patient.

While the invention has been described in connection with what is presently considered to be practical and preferred embodiments thereof, it should be understood that it is not to be limited or restricted to the disclosed embodiments, but rather is intended to cover various modifications, substitutions and combinations within the spirit and scope of the described invention.

The invention claimed is:

1. An apparatus for collecting a urine sample, the apparatus comprising:
    a toilet bowl having a toilet seat;
    a receptacle;
    a flexible sealable urine collection container including a closed bottom end and an open top end opposite the closed bottom end for receiving the urine sample;
    an electronically activated mechanism that moves the urine collection container from the receptacle to a collection location in communication with the toilet bowl such that urine directed into the toilet bowl can be received into the open top end of the urine collection container when the urine collection container is at the collection location; and
    a clamp adapted to clamp the urine collection container to seal urine from the urine sample received therein;
    wherein the clamp comprises at least three pairs of sealing elements, each pair of sealing elements being adapted to cooperate to form one of at least three seals on the urine collection container above the closed bottom end; and
    wherein the clamp is adapted to clamp the urine collection container to seal the urine from the urine sample received therein into at least three discrete sealed portions above the closed bottom end.

2. The apparatus of claim 1, wherein the urine collect or container comprises at least one drain spout to drain off urine that exceeds a pre-determined volume.

3. The apparatus of claim 1, wherein the urine collection container comprises two drain spouts to drain off urine that exceeds a pre-determined volume.

4. The apparatus of claim 1, wherein the receptacle comprises an opening adapted to remove the sealed portions of the urine collection container from the receptacle.

5. The apparatus of claim 4, further comprising a ramp leading to the opening.

6. The apparatus of claim 5, further comprising a door disposed at the opening.

7. The apparatus of claim 1, wherein the clamp comprises two pivoting arms.

8. The apparatus of claim 1, further comprising a printer disposed within the receptacle for printing a patient indicia on one or more of the discrete sealed portions of the urine collection container.

9. The apparatus of claim 1, further comprising a trash receptacle.

10. The apparatus of claim 1, wherein the urine collection container comprises an elongated, flexible, sealable plastic bag.

* * * * *